United States Patent [19]

Kmentt

[11] Patent Number: 5,008,304

[45] Date of Patent: Apr. 16, 1991

[54] ORTHODONTIC APPLIANCE ADHESIVE

[76] Inventor: Bradley A. Kmentt, 2616 Mayfield Rd., No. 2, Cleveland Heights, Ohio 44106

[21] Appl. No.: 353,620

[22] Filed: May 17, 1989

[51] Int. Cl.$^5$ .............................................. C08J 7/00
[52] U.S. Cl. .................................. 523/118; 523/120; 523/213; 523/214; 523/223
[58] Field of Search ............... 523/118, 120, 213, 214, 523/223

[56] References Cited

U.S. PATENT DOCUMENTS 3,936,402  2/1976  Keegan et al. ...................... 523/120
4,239,113  12/1980  Gross et al. ......................... 523/118
4,512,743  4/1985  Santucci et al. .................... 523/118

Primary Examiner—V. Millin
Attorney, Agent, or Firm—Renner, Kenner, Greive, Bobak, Taylor & Weber

[57] ABSTRACT

An orthodontic appliance adhesive has a plurality of glass spheres maintained therein. The glass spheres are coated with a release agent which repels the resin of the adhesive, causing the glass spheres to define effective voids within the adhesive when it is cured. These voids facilitate fracture of the adhesive composite. The beads further provide for a uniform spacing between an orthodontal bracket and a tooth when the adhesive is used for such bonding.

12 Claims, 1 Drawing Sheet

ORTHODONTIC APPLIANCE ADHESIVE

TECHNICAL FIELD

The invention herein resides in the art of orthodontics and, more particularly, to a novel adhesive for securing an orthodontic bracket to a tooth and assuring the subsequent removal of the same without damage to the tooth.

BACKGROUND ART

The use of orthodontic appliances, commonly known as "braces," for achieving proper alignment of teeth has been well known and practiced for many years. The realignment of teeth through orthodontic practices is generally desirable to assure a proper "bite" by an individual to assure that food is properly chewed before being passed to the digestive system. Further, such realignment of teeth has been found to be most desirable for aesthetic reasons.

Previously, metal brackets have been secured to the teeth by means of bands or the like. In recent years, however, direct bonding of the brackets or orthodontic appliances onto the dentition have revolutionized the orthodontic practice. Direct bonding offers several advantages over conventional orthodontic bands. Among these are improved aesthetics, improved hygiene and gingival health, ease of manipulation and placement, and reduced decalcification. The invention herein relates to such direct bonding techniques. Direct bonding typically requires an etching of the tooth enamel to change the surface properties of the enamel from low energy hydrophobic to high energy hydrophilic which increases the surface tension and wetability. Bonding of adhesive composite resins to the etched enamel is achieved by mechanical interlocking with the etched surface.

The most commonly used bonding adhesives for orthodontics are acrylate and diacrylate resins such as Bis GMA. These adhesive systems consist of two parts; a low viscosity unfilled sealing resin and a highly filled paste. Sealing resins are used for a variety of reasons, but, primarily to facilitate wetting and penetration of the etched enamel surface, and as a coupling agent to provide chemical union between the surface and highly filled paste. Sealant resins prevent marginal leakage which can cause bond failure, and they prevent decalcification around the periphery of the bracket base.

The adhesive pastes have an inorganic filler content which varies in the range of 60–80% in weight. Conventional filling materials have quartz particles that lack uniformity in size and shape, or recently, marble shaped silica glass beads having a diameter of approximately 5 microns. The glass fillers are specially treated with silane. Three silane coupling agents are currently in use: gamma-aminopropyltriethoxysilane, vinyltriethoxysilane, and gamma-methacryloxypropyltrimethoxysilane. The latter is most commonly used. An important feature of the silane coating on the glass fillers is to the facilitate bonding between the glass filler particles and the organic matrix of the composite to give the material strength.

A dental composite is a combination of at least two chemically different materials in which a large amount of inorganic filler has been added to the resin matrix. Highly filled diacrylate resins have been shown to produce superior bond strengths. Curing of composite resins can be accomplished chemically with tertiary amine-benzoyl peroxide, or by using a light source to form cross-linked thermoset resin. Chemically cured composites have two adhesive pastes. When the catalyst and base pastes are mixed, polymerization results in cross-linkage, creating a three-dimensional combination that has increased strength, hardness, and dimensional stability. Ultra-violet light has been used to cure filled cross-linked thermoset diacrylate resin. However, such light is poorly transmitted by the tooth structure and requires a long exposure to cure the resin adhesive. Harmful side affects from such radiation is well documented. Recently, a catalyst system for polymerization of diacrylate resin which depends on visible light for activation has been developed. The wave length for visible light curing is in the range of 440–480 nm and does not present any potentially harmful side affects. It is well transmitted by the tooth and, consequently, the exposure time for curing the composite has been dramatically reduced to around 40 seconds.

Chemically cured composite systems have several disadvantages. A major drawback is the inability to manipulate the setting time. Polymerization begins immediately upon mixing and the material sets rapidly once mixing is complete. The working time is restricted and this limits the number of brackets that can be placed with one mix. Mechanical mixing of the two pastes often traps air in the composite resin which inhibits polymerization and concentrates stress that can further weaken the adhesive bond. When the bracket is placed, excess composite is often difficult to remove. Plaque readily accumulates on the excess composite, contributing to gingival irritation and possible enamel decalcification.

Visible light cured composites offer several advantages over the conventional chemically cured adhesives. A major advantage is the command set. The setting time can be controlled and the resin will only set when exposed to an intense white light source. Incorporation of air into the composite is less likely because there is no mixing involved. When using light activated materials, a slight excess of adhesive can be placed on the bracket base. When the bracket is seated, the excess composite extrudes and the possibility of voids at the edge of the bracket is reduced. The flash can easily be removed from around the bracket before curing is initiated. The viscosity of the light cured materials does not change and this makes manipulation predictable. Unlimited working time allows for ideal bracket positioning which is critical with straight wire appliances. Sealant can be placed on the base of the metal brackets to eliminate air from the retentive mechanism and allow for complete penetration of resin into the retentive areas.

The invention described hereinafter can be used with any type of orthodontal resin or adhesive, but the state of the art is directed to the use of visible light cured composites as just discussed. Accordingly, the invention will be described with respect to implementation with such composites, but without restriction or reservation to the implementation thereof with other bonding adhesives.

It is well known that interfacial and internal defects have a tendency to reduce bond strength. Air voids incorporated into the resin during mixing weaken the adhesive composite. Stress concentration may arise at these sites during polymerization of the resin, which may propagate along the defects during application of tensile and sheer stresses. Such weakening is well known and documented, as is the adverse affect of such air voids on polymerization.

The composite film thickness between the bracket and the tooth is an important factor which is often overlooked. A minimum layer of film is important for obtaining a maximum adhesion. A thicker adhesive interface produces more imperfections, greater polymerization shrinkage, and may fracture more readily. Uneven resin thicknesses can lead to residual stress in the adhesive film. It has been found that as the polymerization gap decreases, shear bond strength increases in an exponential relationship. Controlling the film thickness during bonding is extremely important, but heretofore has been unachieved.

The bonding of metal orthodontic attachments is primarily through mechanical retention between the bracket base and adhesive interface. Since the inception of direct bonding, metal brackets have been the most popular because of their mechanical advantages and familiarity among practioners. Several base designs of metal brackets have been manufactured; of these, mesh and groove based designs are the most popular. It is now accepted that mesh metal brackets provide adequate retention.

New ceramic brackets are renowned for their hardness, thermal integrity, and resistance to chemical erosion. They offer a distinct aesthetic advantage over conventional stainless steel brackets. However, ceramics have low fracture toughness and are therefore more prone to fracture. Typically, ceramic brackets are made of aluminum oxide (alumina). They are chemically inert and do not directly adhere to bonding adhesives. In order to solve this problem, ceramic bracket bases are available with two retentive mechanisms. The bases are either treated with a coupling agent that will chemically bond to the composite resin, or they have a combination of chemical coupling with mechanical undercuts for retention. The ceramic bases are typically treated with a silane coupling agent similar to the bonding agent applied to the glass fillers to provide for coupling between the glass fillers and the organic matrix of the adhesive composite.

While there are various types of orthodontic brackets presently used, metal or ceramic, the invention herein is adapted for implementation with either, having particular applicability to the ceramic brackets which are presently the trend in the art.

With reference now to FIG. 1 the prior art structure for adhering a bracket to a tooth may be seen. As shown, a bracket and tooth assembly is designated generally by the numeral 10. The bracket 12 whether metallic or ceramic, is adhered by means of an adhesive composite 14 to the enamel layer 16 of the tooth 18. The glass silane-coated particles 20 are interposed in the adhesive composite 14 to enhance bonding strength. Of course, metal wires or other tensioning means are interconnected between the grooves of the brackets 12 from one tooth to another to obtain the desired movement and alignment of the teeth.

Once the orthodontic treatment requiring the "braces" and requisite brackets 12 has been completed, it is important that the brackets 12 be readily removed from the teeth 18 without damage to the enamel surface 16. Typical debracketing instruments remove the appliance by application of both shear and tensile stresses. The bracket is removed, yet, considerable composite still remains on the tooth. Tensile forces transmit a significant amount of stress to the enamel layers 16 and are not recommended. If crazing lines are present in the enamel, tensile debonding forces are quite likely to pull enamel off with the bracket if fracture is at the enamel-bracket interface.

The issue of debonding ceramic brackets has raised a great deal of concern. Silane treatment of the ceramic base produces exceptional bond strengths which exceed the fracture toughness of the material. Debonding stresses can be shifted from the bracket/composite interface to the composite/enamel interface. Adhesive bond failures at the composite/tooth interface have been reported to be potentially harmful. Cohesive failure of the enamel is also not desirable. Ceramic brackets are likely to fail at these locations. Rigid, brittle ceramics have little ability to absorb stresses. Since the bracket/adhesive bond is dramatically enhanced by virtue of silane coupling, failure will usually occur in the ceramic, within the adhesive, or in the enamel. A sudden impact load is more likely to cause failure within the more brittle ceramic and enamel than in the polymeric bonding material 14.

Squeezing the tie wings of a ceramic bracket with a pair of pliers will undoubtedly cause ceramic failure. Similarly, use of a lift-off bracketing instrument will result in tensile failure of the fragile tie wings. Only diamond and pure carbon crystals are hard enough to cut the aluminum oxide bracket. If a portion of the bracket remains on the tooth after the debonding operation, it must then be ground off with a grinding wheel of diamond or the like, the same being a delicate operation, generating significant heat, and risking tooth damage. Further, ceramic brackets are not conducive to electrothermal debracketing techniques.

Ceramic brackets are frequently removed with a shear force applied by wedging between the enamel surface and bracket base with the blades of debonding pliers or ligature cutters. This technique leaves the least amount of residual adhesive on the tooth, however, significant enamel damage has been documented with this type of instrumentation. Bracket fractures are prevalent. Harm can result if one aspirates or swallows a ceramic fragment.

Because of the debonding problems associated with ceramic brackets, many practioners are reluctant to use them in their practices. Reports of enamel damage during the course of treatment and enamel failures while debonding are becoming prevalent. An improvement in the bonding of the ceramic brackets to the tooth enamel is required.

DISCLOSURE OF INVENTION

In light of the foregoing, it is a first aspect of the invention to provide an orthodontic appliance adhesive which facilitates debonding of the bracket from the tooth.

Another aspect of the invention is the provision of an orthodontic appliance adhesive in which the fracture of the adhesive upon debonding occurs through the adhesive or at the interfacial areas between the adhesive and the bracket or the enamel layer.

Another aspect of the invention is the provision of an orthodontic appliance adhesive which assures a consistent and predictable film layer of the adhesive between the bracket and the tooth.

Yet another aspect of the invention is the provision of an orthodontic appliance adhesive which firmly retains the bracket to the tooth during the treatment period but is easily removed at the end of such treatment.

Yet an additional aspect of the invention is the provision of an orthodontic appliance adhesive which is conducive to implementation with presently existing orthodontic brackets.

The foregoing and other aspects of the invention which will become apparent as the detailed description proceeds are achieved by an adhesive composite, comprising; and adhesive materials; and a plurality of release particles suspended within said adhesive material, said particles have an affinity for repelling said adhesive material and remaining substantially unattached thereto.

Other aspects of the invention are attained by an orthodontal adhesive, comprising; an adhesive resin taken from the group of acrylate and diacrylate resins; and a plurality of release particles within said adhesive resin, said release particles being substantially unadhered to said adhesive resin when said adhesive resin is cured.

Still further aspects of the invention are obtained by an orthodontal appliance. comprising of: a bracket; a tooth surface to which said bracket is to be adhered; and an adhesive layer interposed between said tooth and bracket, said adhesive comprising: a plurality of release particles maintained within said adhesive layer, said release particles establishing affective voids within said adhesive for facilitating fracture of said adhesive layer.

DESCRIPTION OF DRAWING

For a complete understanding of the objects, techniques and structure of the invention reference should be had to the following detailed description and accompanying drawings wherein.

BEST MODE FOR CARRYING OUT THE INVENTION

Figure 1:
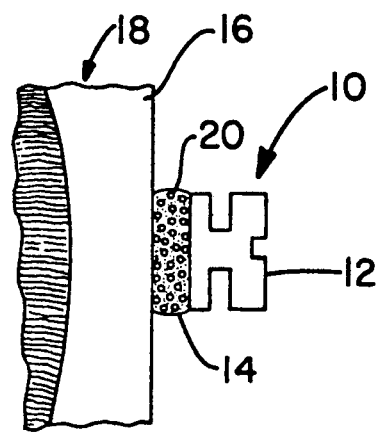
FIG. 1 is an illustrative elevational view of an orthodontic bracket adhered to a tooth according to the prior art.

The primary purpose of this invention is to provide an orthodontic composite that will predictably fail in a predetermined mode, is inherently weakened, and may facilitate debonding of ceramic brackets when compared to existing composites. Composite materials, particularly brittle materials, generally fail due to stress concentration about surface or internal defects. Materials can, therefore, be designed to fail at particular stresses less than their inherent strength by introducing flaws of predetermined size and shape. An estimation of the defect size that will result in failure at a given critical stress is given by the Griffith equation: $R^2 = (2ES/piC)$, where R is the critical tensile stress necessary for failure, E is the modules of elasticity of the material, S is the material's effective surface energy, and C is the effective radius of the defect size necessary for failure at the interface between two different materials.

In accordance with the invention, the defect to be introduced into the adhesive composite is in the form of barium glass beads which are coated with an appropriate release agent such as dimethylsiloxane or silicone oil. Such a release agent has no affinity of attraction for, but repels, the adhesive mix, of whatever type, but preferably of the acrylate or diacrylate resin type. Indeed, the release agent causes the glass beads to be hydrophobic. The release agent prevents the beads from coupling with the organic composite matrix, and insures that the glass beads or other such coated particles will essentially be voids, thereby reducing the composite strength.

The desired bead size for the necessary composite failure may be estimated from the Griffith equation, referenced above. It has been found that glass beads having a diameter greater than 30 microns, and preferably on the order of 50-120 microns are suitable for the intended purpose. The beads may be coated with dimethylsiloxane or silicone oil by means of an appropriate bath, after which they are drained through a filter paper and air dried.

The treated glass beads may then be introduced into the adhesive composite of the types mentioned earlier herein in concentrations of 5-20%, and preferably 5-10% by volume. The beads are uniformly mixed within the adhesive composite to obtain a uniform distribution of the same throughout the composite. The resulting composite may then be formed into a bar having a square or rectangular cross section as designated by numeral 22 in FIG. 2. As shown in the drawing, the beads 24, having a release coating thereon, are uniformly disbursed throughout the composite. The bar 22 may then be placed upon the supports 26 with a force F being applied to the top of the bar 22 midway between the supports 26. This 3-point flexure strength test allows a determination as to the force F which results in fracture. Knowing the desired fracture force F, confirmation of adherence to the Griffith equation can then be determined. Of course, the fracture force F will be indicative of the strength of the composite 22 which will result in debonding of a bracket from a tooth without damage to the tooth.

Figure 3:
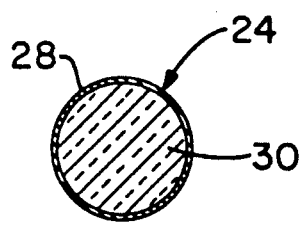
FIG. 3 is a cross sectional view of a glass bead of the type maintained within the adhesive composite of the invention.

As shown in FIG. 3, the release coating 28 constitutes a thin film on the glass sphere 30. It will be understood that the layer 28 may be extremely thin in comparison to the size of the sphere 30, being sufficient to cause the bead 24 to be hydrophobic since that its placement into the composite 22 will affectively define voids therein.

Figure 4:
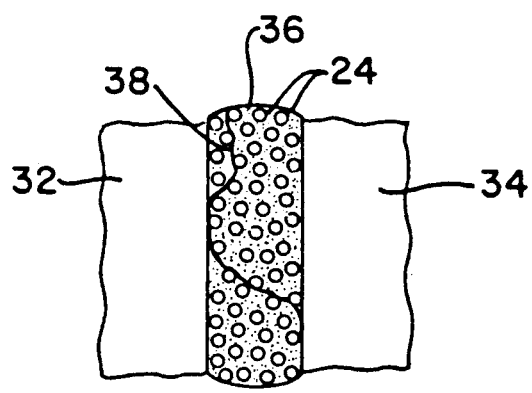
FIG. 4 is a side elevational view of two elements secured by the adhesive composite of the invention.

As shown in FIG. 4, a pair of members 32,34 may be bonded together by means of the adhesive 36 having the coated beads 24 dispersed therein, as just discussed. In attempting to separate the members 32,34 from each other, whether by the application of tensile or shear forces, the fracture of the adhesive composite 36 will typically follow the path of least strength within the adhesive 36. The voids defined by the coated beads 24 disbursed throughout the adhesive composite 36 helped to define this weakened path. As shown, a fracture line 38 will typically follow the beads. The fracture line 38 may pass solely through the composite 36 (cohesive failure), or at the interface of the members 32,34 with the adhesive composite layer 36 (adhesive failure), or a combination of the two. In either event, with the composite 36 having been compounded to have a fracture strength less than that of the members 32,34 fracturing of those members will be minimized or eliminated.

Figure 2:
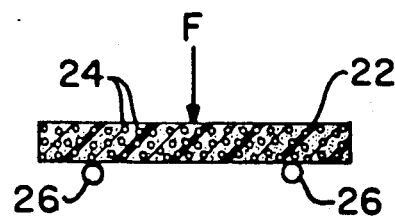
FIG. 2 is a front prospective view of a specimen of an adhesive composite according the invention, under load.
Figure 5:
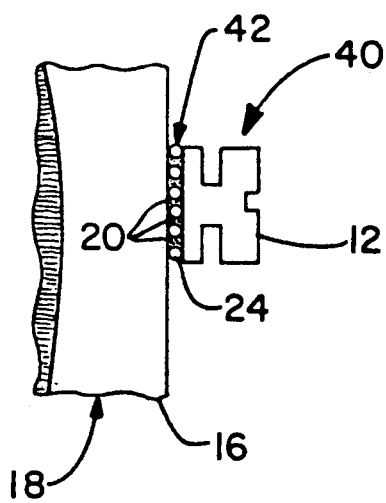
FIG. 5 is a side elevational view of a bracket attached to a tooth using the composite adhesive of the invention.

The application of the concept of FIG. 4 to the retention and debonding of an orthodontal bracket with respect to a tooth is shown in FIG. 5. Here, a bracket and tooth assembly adhered according to the invention is designated generally by the number 40. A layer of adhesive composite of the invention 42, containing a plurality of coated beads 24 and silane coated filling particles 20 is interposed between the bracket 12 and the enamel layer 16 of a tooth 18. The adhesive composite 42 has been appropriately cured, either chemically or by application of visible light, depending upon the type of resin employed. With the sphere size 24 having been appropriately chosen by means of the Griffith equation, as confirmed by a testing of the characteristic fracture force F as shown in FIG. 2, the bracket 12 may be readily debonded from the tooth 18 without damage to the enamel layer 16. The fracture of the adhesive composite 42 will be along the weakened areas defined by the effective voids generated by the coated beads 24. As in the case of FIG. 4, the fracture may occur at the interface of the adhesive composite 42 with the bracket 12 or enamel layer 16, or simply through the composite 42 itself. In either event, the totality of the bracket 12 is separated from the tooth 18 without damage to either. Further, no residue of the bracket 12 remains attached to the tooth 18. Any residue of the adhesive composite 42 remaining on the enamel layer 16 of the tooth 18 may be easily scraped or buffed away.

It should be appreciated that a further benefit of the composite 42 is the ability to obtain an adhesive layer of controlled thickness. The beads 24, having a fixed preferred diameter of 50–120 microns, serve as spacers between the tooth 18 and the bracket 12. The composite adhesive 42 is applied to either the bracket 12, tooth 18, or both. The bracket 12 is then firmly pressed against the tooth 18, with the composite adhesive being extruded from the sides. This residue may be scrapped or otherwise removed prior to cure. The film thickness of the composite adhesive 42 is then equal the diameter of the beads 24.

Figure 6:
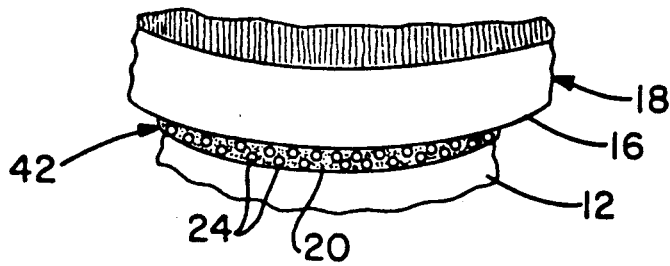
FIG. 6 is a top sectional view of the assembly of FIG. 5.

The uniform thickness of the adhesive film can be obtained even though the tooth 18 has a typically convex surface, which is to mate with a concave surface of the bracket 12. This feature is shown in the top sectional view of FIG. 6. The effective radius of curvature of the convex tooth surface may not be the same as the effective radius of curvature of the concave bracket surface. As a result, when the bracket 12 is pressed against the tooth 18, the adhesive composite 42 will be extruded to a single bead thickness at the edges of the bracket 12, while the thickness of the adhesive composite 42 may be somewhat greater therebetween. While the adhesive layer may not be of uniform thickness, its thickness is at least minimized, assuring maximum adhesive integrity.

It will readily be appreciated by those skilled in the art that the concept of the invention is to provide voids or areas of stress concentration within an adhesive composite to assure a predictable fracture line therethrough when debonding is desired. The brittle nature of orthodontic adhesives assures that fracture will occur at a weak point, defined by a bead 24, and rapidly propagate through the brittle material, typically from bead to bead or bead to interface. It will further be appreciated by those skilled in the art that the beads 24 need not be spheres, but can have any of various geometric shapes or configurations. However, spherical beads or other generally rounded configurations are preferred to eliminate the protrusion of a rough or jagged edge which might be engaged in brushing. It will further be appreciated that the beads 24 need not be glass beads, but can be of any suitable material such as quartz, mica, or suitable synthetic material such as plastic. Glass has been found to be particularly suitable, having a coefficient of thermal expansion close to that of enamel. Yet further, those skilled in the art will readily appreciate that the concept of the invention can be expanded to any of various types of adhesives, not just orthodontal adhesives. Indeed, the controlled introduction of voids or weakened zones within adhesives or cements of any of numerous types can be readily perceived.

Thus it can be seen that the objects of the invention have been satisfied by the structure presented hereinabove. While in accordance with the patent statutes, only the best mode and preferred embodiment of the invention has been presented and described in detail, the invention is not limited thereto or thereby. Accordingly, for an appreciation for the true scope and breadth of the invention references should be made to the following claims:

What is claimed is:

1. An adhesive composite, comprising:
   an adhesive material; and
   a plurality of release particles suspended within said adhesive material, said particles being coated with a hydrophobic coating for repelling said adhesive material to remain substantially unattached thereto.

2. The adhesive composite according to claim 1, wherein said hydrophobic coating is selected from the group of dimthylsiloxane and silicone oil.

3. The adhesive composite according to claim 2, wherein said release particles are selected from the group of glass, quartz, and silica.

4. The adhesive composite according to claim 2, wherein said release particles comprise spherical glass beads.

5. The adhesive composite according to claim 4, wherein said glass beads have a diameter of 50–120 microns.

6. The adhesive composite according to claim 2, wherein said adhesive material comprises a low viscosity unfilled sealing resin in a highly filled paste.

7. The adhesive composite according to claim 1, wherein said adhesive material is selected from a group of acrylate and diacrylate resins.

8. An orthodontal adhesive, comprising:
   an adhesive resin taken from the group of acrylate and diacrylate resins; and
   a plurality of release particles within said adhesive resin, said release particles being substantially unadhered to said adhesive resin when said adhesive resin is cured.

9. The orthodontal adhesive according to claim 8, wherein said release particles are coated with a release agent.

10. The orthodontal adhesive according to claim 9, wherein said release agent is hydrophobic.

11. The orthodontal adhesive according to claim 10, wherein said release agent is selected from the group of dimethylsiloxane and silicone.

12. The orthodontal adhesive according to claim 11, wherein said release particles are spherical, having a diameter of 50–120 microns.

* * * * *